United States Patent
Fimreite

(10) Patent No.: US 6,756,405 B2
(45) Date of Patent: Jun. 29, 2004

(54) CONJUGATED LINOLEIC ACID POWDER

(75) Inventor: Duane Fimreite, Chicago, IL (US)

(73) Assignee: Natural ASA (NO)

(*) Notice: Subject to any disclaimer, the term of this patent is extended or adjusted under 35 U.S.C. 154(b) by 260 days.

(21) Appl. No.: 09/836,788

(22) Filed: Apr. 17, 2001

(65) Prior Publication Data

US 2002/0013365 A1 Jan. 31, 2002

Related U.S. Application Data

(60) Provisional application No. 60/198,487, filed on Apr. 18, 2000.

(51) Int. Cl.$^7$ .................. A61K 31/22; A61K 31/20; A61K 7/00; A61K 31/231; A61K 35/78
(52) U.S. Cl. .................. 514/560; 514/558; 514/546; 514/549; 424/439
(58) Field of Search .................. 514/560, 558, 514/546, 549; 424/439, 770, 727, 757

(56) References Cited

U.S. PATENT DOCUMENTS

| | | | |
|---|---|---|---|
| 2,242,230 A | 5/1941 | Burr | 260/398 |
| 2,350,583 A | 6/1944 | Bradley | 260/195.6 |
| 3,162,658 A | 12/1964 | Baltes et al. | 260/405.6 |
| 3,278,567 A | 10/1966 | Rathjen | 260/405.6 |
| 3,729,379 A | 4/1973 | Emken | 195/30 |
| 4,164,505 A | 8/1979 | Krajca | 260/405.6 |
| 4,232,052 A * | 11/1980 | Nappen | 426/601 |
| 4,381,264 A | 4/1983 | Struve | 260/405.6 |
| 5,017,614 A | 5/1991 | Pariza et al. | 514/558 |
| 5,070,104 A | 12/1991 | Pariza et al. | 514/549 |
| 5,208,356 A | 5/1993 | Pariza et al. | 554/79 |
| 5,288,619 A | 2/1994 | Brown et al. | 435/134 |
| 5,428,072 A | 6/1995 | Cook et al. | 514/560 |
| 5,430,066 A | 7/1995 | Cook et al. | 514/558 |
| 5,468,887 A | 11/1995 | Gupta | 554/169 |
| 5,510,110 A * | 4/1996 | Puritch et al. | 424/421 |
| 5,554,646 A | 9/1996 | Cook et al. | 514/560 |
| 5,562,913 A * | 10/1996 | Horrobin | 424/401 |
| 5,585,400 A | 12/1996 | Cook et al. | 514/560 |
| 5,670,540 A * | 9/1997 | Horrobin et al. | 514/549 |
| 5,674,901 A | 10/1997 | Cook et al. | 246/452 |
| 5,725,873 A | 3/1998 | Cook et al. | 424/442 |
| 5,760,082 A * | 6/1998 | Cook et al. | 514/560 |
| 5,760,083 A * | 6/1998 | Cook et al. | 514/560 |
| 5,804,210 A | 9/1998 | Cook et al. | 424/440 |
| 5,814,663 A * | 9/1998 | Cook et al. | 514/560 |
| 5,827,885 A | 10/1998 | Cook et al. | 514/558 |
| 5,851,572 A * | 12/1998 | Cook et al. | 426/2 |
| 5,855,917 A | 1/1999 | Cook et al. | 424/502 |
| 5,856,149 A | 1/1999 | Pariza et al. | 435/134 |
| 5,885,594 A * | 3/1999 | Nilsen et al. | 424/401 |
| 5,919,451 A | 7/1999 | Cook et al. | |
| 5,986,116 A | 11/1999 | Iwata et al. | 554/126 |
| 6,015,833 A | 1/2000 | S.ae butted.b.o slashed. et al. | 514/558 |
| 6,019,990 A | 2/2000 | Remmereit | 424/401 |
| 6,034,132 A | 3/2000 | Remmereit | 514/560 |
| 6,042,869 A | 3/2000 | Remmereit | 426/630 |
| 6,060,514 A * | 5/2000 | Jerome et al. | 514/560 |
| 6,160,140 A | 12/2000 | Bhaggan et al. | 554/126 |
| 6,184,009 B1 * | 2/2001 | Cain et al. | 435/134 |
| 6,203,843 B1 | 3/2001 | Remmereit | 426/630 |
| 6,214,372 B1 | 4/2001 | Jerome et al. | 424/439 |
| 6,225,486 B1 * | 5/2001 | Saebo et al. | 554/221 |
| 6,242,621 B1 | 6/2001 | Jerome et al. | 554/224 |
| 6,251,478 B1 * | 6/2001 | Pacifico et al. | 427/213.3 |
| 6,271,404 B1 | 8/2001 | Bhaggan et al. | 554/126 |
| 6,333,353 B2 | 12/2001 | Saebo et al. | 514/558 |
| 6,344,230 B2 | 2/2002 | Remmereit | 426/601 |
| 6,380,409 B1 | 4/2002 | Saebo et al. | 554/126 |
| 6,410,761 B1 | 6/2002 | Saebo et al. | 554/126 |
| 6,432,469 B1 | 8/2002 | Remmereit | 426/630 |
| 6,440,931 B1 | 8/2002 | Remmereit et al. | 514/3 |
| 6,465,666 B2 | 10/2002 | Jerome et al. | 554/224 |
| 6,524,527 B2 * | 2/2003 | Fimreite et al. | 426/648 |

FOREIGN PATENT DOCUMENTS

| | | |
|---|---|---|
| DE | 199 14 279 | 3/1999 |
| DE | 199 22 942 | 5/1999 |
| DE | 199 40 751 | 8/1999 |
| DE | 199 40 752 | 8/1999 |
| EP | 779033 A1 | 6/1997 |
| EP | 0 950 410 | 3/1999 |
| GB | 558881 | 1/1944 |
| JP | 2000-050814 * | 2/2000 |
| JP | 2000050851 | 2/2000 |
| WO | WO 96/38137 | 5/1996 |
| WO | WO 96/34855 | 11/1996 |
| WO | WO 97/18320 | 5/1997 |
| WO | WO 9737546 | 10/1997 |
| WO | WO 97/37546 | 10/1997 |
| WO | WO 9746230 | 11/1997 |
| WO | WO 97/46118 | 12/1997 |
| WO | WO 98/05318 | 2/1998 |
| WO | WO 98/05319 | 2/1998 |
| WO | WO 98/49129 | 11/1998 |
| WO | WO 00/67596 | 11/2000 |
| WO | WO 01/44485 | 2/2001 |
| WO | WO 01/53512 | 7/2002 |

OTHER PUBLICATIONS

"Conjugated Linoleic Acid in Canadian Dairy and Beef Products", Ma et al., Journal of Agriculture and Food Chemistry, 1999, 47(5), 1956–1960.*

Cowan, "Isomerization and Trans–Esterifiation," *JAOCS* 72:492–99 (1950).

Christie et al., "Isomers in Commerical Samples of Conjugated Linoleic Acid," *JAOCS* 74 (11):1231 (1997).

Kepler et al., *J. Biol. Chem.* 127(6):1055–60 (1997).

Belury, "Conjugated Dienoic Linoleate: A Polyunsaturated Fatty Acid with Unique Chemoprotective Properties," *Nut. Rev.* 53(4):83–9 (1995).

(List continued on next page.)

*Primary Examiner*—Zohreh Fay
*Assistant Examiner*—Brian Kwon
(74) *Attorney, Agent, or Firm*—Medlen & Carroll, LLP

(57) ABSTRACT

A powder containing a high amount of conjugated linoleic acid or other oil is provided. The powder contains either triglycerides containing CLA, free fatty acids of CLA, or alkylesters of CLA, or another desired oil. The powder is free flowing and has good organoleptic properties. The powder may be used as a dietary supplement or combined with foodstuffs to form a food product suitable for consumption by animals or humans.

15 Claims, No Drawings

OTHER PUBLICATIONS

Ha et al., *Cancer Res.*, 50:1097 (1991).
Birt et al., *Cancer Res.*, 52:2035–s (1992).
Ip, *Am. J. Clin. Nutr.* 66(6):1523s (1997).
Sehat et al., Lipids 33(2):217–21 (1998).
Jie, et al., "High–Resolution Nuclear Magnetic Resonance Spectroscopy –Amplification to fatty Acids and Triacylglycerols," *Lipids*32 (10): 1019–34 (1997).
Scholfield and Koritalia, "A Simple Method for Preparation of Methyl trans–10,cis–12 octadecadienoate," *JOACS*47(8):303 (1970).
Ron Udell, Information About Conjugated Linoleic Acid, published by Soft Gel Technologies Incorporated, 1997.
Sugano et al., "Conjugated Linoleic Acid Modulates Tissue Levels of Chemical Mediators and Immunoglobulins in Rats," *Lipids*, 33(5):521–27 (1998).
Matreya Catalog, 1997, pp. 33–44.
Selin CLA Product Literature, 1/97.
Hudtwalcker & Co. AS Technical Data Sheet, Exact publication date unknown, 1995.
Lipid Technology Newsletter, Peter J. Barnes, Ed., vol. 4, No. 5, pp. 85–86 (Oct, 1998).
Natural Lipids Ltd. AS Technical Data Sheet, Jan. 20 ,1997.
Ciganek, J. of Organic Chemistry, 35:1725 (1970).
Theil et al., "Conjugated Linoleic Acid Improves Performance and Body Composition in Swine", Iowa State University, Midwest Animal Sciences Meeting, 127:61 (1998).
Quinn et al "A Comparison of Modified Tall Oil and Conjugated Linoleic Acid on Growing–Finishing Pig Growth Performance and Carcass Characteristics," Kansas State University and Lonza, Inc., Midwest Animal Sciences Meeting, Abstract 128:61 (1998).
Dugan et al., "The effect of Conjugated Linoleic Acid on Fat to Lean Repartitioning and Feed Conversion in Pigs," *Canadian Journal of Animal Science* 77:723–725 (1997).
Shantha et al.,"Conjugated linoleic Acid Concentrations in Processed Cheese Containing Hydrogen Donors, Iron and Dairy –Based Additives," *Food Chemistry* 47:257–261 (1993).
Bradley et al., "Alkali–Induced Isomerization of Drying Oils and Fatty Acids," *Ind. Eng. Chem.* 34(2):237–242 (1942).
Jie et al., "Synthesis and Nuclear Magnetic Resonance Properties of All Geometrical Isomers of Conjugated Linoleic Acids," *Lipids* 32(10):1041–1044 (1997).

Arcos et al., "Rapid Enzymatic Production of aclglycerols from conjugated linoleic acid and glycerol in the solvent–free system," *Biotechnology Letters* 20:617 (1998).
Holman et al., "Unusual Isomeric Polyunsaturated Fatty Acids in Liver Phospholipids of Rats Fed Hydrogenated Oil," *PNAS* 88:4830–34 (1991).
Radlove et al., "Catalytic Isomerization of Vegetable Oils," *Ind. Eng. Chem.* 38(10):997–1002 (1946).
Sebedio et al., "Linoleic Acid Isomers in Heat Treated Sunflower Oils," *JAOCS* 65(3):362–366 (1988).
Chin et al., "Dietary Sources of Conjugated Dienoic Isomers of Linoleic Acids, a Newly Recognized Class of Anticarcinogens," *J. Food. Comp. Anal.* 5:185–197 (1992).
Park et al., "Effect of Conjugated Linoleic Acid on Body Composition in Mice," *Lipids* 32(8):853–58 (1997).
Berdeau et al., "A Simply Method of Preparation of Methyl *trans*–10, *cis*–12–and *cis*–9,*trans*–11–Octadecadienoates from Methyl Linoleate," *JAOCS* 75:1749–1755 (1998).
Aneja, et al., *J. Dairy Sci.*, 43:231 (1990).
Shanta, et al., *Food Chem.*, 47:257 (1993).
Shanta, et al., *J. Food Sci.*, 60: 695 (1995).
Parodi, et al., *J. Dairy Sci.*, 60: 1550 (1997).
Chin, et al., *J. Food Camp. Anal.*, 5: 185 (1992).
Kepler, et al., *J. Nutrition*, 56: 1191 (1966).
Chin, et al.,*J. Nutrition*, 124: 694 (1994).
Marcel S.F. Lie Ken Jie and J. Mustafa, *Lipids*, 32 (10) 1019–34 (1997).
Banni et al., J. of Lipid Research 42:1056 (2001).
Chuang et al., Lipids 36:139 (2001).
Bretillon et al., Lipids 34:965 (1999).
Janssen et al., Biomedical And Environmental Mass Spectrometry 16:1–6 (1988).
Park et al., Lipids 34:235–241 (1999).
Sebedio et al., Lipids 34:1319–1325 (1999).
Zambell et al., Lipids 35:777–782 (2000).
Blankson et al., American Society for Nutritional Sciences 1–6 (2000).
Yurawecz et al., Lipid 8:277–282 (1999).
Haraldsson, et al., Acta Chem Scanned 45: 723 (1991).

* cited by examiner

CONJUGATED LINOLEIC ACID POWDER

This application claims priority to U.S. Provisional Application 60/198,487, filed Apr. 18, 2000.

FIELD OF THE INVENTION

The present invention relates to the field of human and animal nutrition, and in particular to a novel composition of conjugated linoleic acid (CLA) powder.

BACKGROUND OF THE INVENTION

In 1978, researchers at the University of Wisconsin discovered the identity of a substance contained in cooked beef that appeared to inhibit mutagenesis. The substance was found to be a mixture of positional isomers of linoleic acid (C18: 2) having conjugated double bonds. The c9,t11 and t10,c12 isomers are present in greatest abundance, but it is uncertain which isomers are responsible for the biological activity observed. It has been noted from labeled uptake studies that the 9,11 isomer appears to be somewhat preferentially taken up and incorporated into the phospholipid fraction of animal tissues, and to a lesser extent the 10,12 isomer (Ha, et al., Cancer Res., 50: 1097 [1990]).

The biological activity associated with conjugated linoleic acids (termed CLA) is diverse and complex. At present, very little is known about the mechanisms of action, although several preclinical and clinical studies in progress are likely to shed new light on the physiological and biochemical modes of action. The anticarcinogenic properties of CLA have been well documented. Administration of CLA inhibits rat mammary tumorigenesis, as demonstrated by Birt, et al., Cancer Res., 52: 2035s [1992]. Ha, et al., Cancer Res., 50: 1097 [1990] reported similar results in a mouse forestomach neoplasia model. CLA has also been identified as a strong cytotoxic agent against target human melanoma, colorectal and breast cancer cells in vitro. A recent major review article confirms the conclusions drawn from individual studies (Ip, Am. J. Clin. Nutr., 66 (6 Supp): 1523s [1997]).

Although the mechanisms of CLA action are still obscure, there is evidence that some component(s) of the immune system may be involved, at least in vivo. U.S. Pat. No. 5,585,400 (Cook, et al., incorporated herein by reference), discloses a method for attenuating allergic reactions in animals mediated by type I or TgE hypersensitivity by administering a diet containing CLA. CLA in concentrations of about 0.1 to 1.0 percent was also shown to be an effective adjuvant in preserving white blood cells. U.S. Pat. No. 5,674,901 (Cook, et al.), incorporated herein by reference, disclosed that oral or parenteral administration of CLA in either free acid or salt form resulted in elevation in CD-4 and CD-8 lymphocyte subpopulations associated with cell-mediated immunity. Adverse effects arising from pretreatment with exogenous tumor necrosis factor could be alleviated indirectly by elevation or maintenance of levels of CD-4 and CD-8 cells in animals to which CLA was administered. Finally, U.S. Pat. No. 5,430,066, incorporated herein by reference, describes the effect of CLA in preventing weight loss and anorexia by immune stimulation.

Apart from potential therapeutic and pharmacologic applications of CLA as set forth above, there has been much excitement regarding the use of CLA nutritively as a dietary supplement. CLA has been found to exert a profound generalized effect on body composition, in particular redirecting the partitioning of fat and lean tissue mass. U.S. Pat. No. 5,554,646 (Cook, et al.), incorporated herein by reference, discloses a method utilizing CLA as a dietary supplement in which pigs, mice, and humans were fed diets containing 0.5 percent CLA. In each species, a significant drop in fat content was observed with a concomitant increase in protein mass. It is interesting that in these animals, increasing the fatty acid content of the diet by addition of CLA resulted in no increase in body weight, but was associated with a redistribution of fat and lean within the body. Another dietary phenomenon of interest is the effect of CLA supplementation on feed conversion. U.S. Pat. No. 5,428,072 (Cook, et al., incorporated herein by reference), provided data showing that incorporation of CLA into animal feed (birds and mammals) increased the efficiency of feed conversion leading to greater weight gain in the CLA supplemented animals. The potential beneficial effects of CLA supplementation for food animal growers is apparent.

Another important source of interest in CLA, and one which underscores its early commercial potential, is that it is naturally occurring in foods and feeds consumed by humans and animals alike. In particular, CLA is abundant in products from ruminants. For example, several studies have been conducted in which CLA has been surveyed in various dairy products. Aneja, et al., J. Dairy Sci., 43: 231 [1990] observed that processing of milk into yogurt resulted in a concentration of CLA (Shanta, et al., Food Chem., 47: 257 [1993]) showed that a combined increase in processing temperature and addition of whey increased CLA concentration during preparation of processed cheese. In a separate study, Shanta, et al., J. Food Sci., 60: 695 [1995] reported that while processing and storage conditions did not appreciably reduce CLA concentrations, they did not observe any increases. In fact, several studies have indicated that seasonal or interanimal variation can account for as much as three fold differences in CLA content of cows milk (See e.g., Parodi, et al., J. Dairy Sci., 60: 1550 [1977]). Also, dietary factors have been implicated in CLA content variation, as noted by Chin, et al., J. Food Camp. Anal., 5: 185 [1992]. Because of this variation in CLA content in natural sources, ingestion of prescribed amounts of various foods will not guarantee that the individual or animal will receive the optimum doses to ensure achieving the desired nutritive effect.

Linoleic acid is an important component of biolipids, and comprises a significant proportion of triglycerides and phospholipids. Linoleic acid is known as an "essential" fatty acid, meaning that the animal must obtain it from exogenous dietary sources since it cannot be autosynthesized. Incorporation of the CLA form of linoleic acid may result in a direct substitution of CLA into lipid positions where unconjugated linoleic would have migrated. However, this has not been proven, and some of the highly beneficial but unexplained effects observed may even result from a repositioning of CLA within the lipid architecture at sites where unconjugated linoleic acid would not have otherwise migrated. It is now clear that one source of animal CLA, especially in dairy products, comes from the biochemical action of certain rumen bacteria on native linoleic acid, first isomerizing the linoleic acid to CLA, and then secreting it into the rumen cavity. Kepler, et al., J. Nutrition, 56: 1191 [1966] isolated a rumen bacterium, *Butyrivibrio fibrisolvens*, which catalyzes formation of 9,11-CLA as an intermediate in the biohydrogenation of linoleic acid. Chin, et al., J. Nutrition, 124: 694 [1994] further found that CLA found in the tissues of rodent was associated with bacteria, since corresponding germ-free rats produced no CLA.

In the development of a defined commercial source of CLA for both therapeutic and nutritional application, a process for generating CLA that is palatable and that can be incorporated as a component in food products is needed. CLA provided as a free fatty acid oil often has an unpleasant taste and its ingestion may cause undesired belching in some individuals. Furthermore, free fatty acid oils may be difficult to incorporate into food products, especially dried food products. Accordingly, what is needed in the art are CLA compositions having good organoleptic and formulation properties.

SUMMARY OF THE INVENTION

The present invention relates to the field of human and animal nutrition, and in particular to a novel composition of conjugated linoleic acid (CLA) powder.

In some embodiments, the present invention provides a composition comprising a conjugated linoleic acid moiety and an excipient. The present invention is not limited to any particular conjugated linoleic acid moiety. Indeed, a variety of conjugated linoleic acid moieties are contemplated including, but not limited to, triglycerides, free fatty acids, and alkylesters.

The present invention is not limited to any particular excipient. Indeed, a variety of excipients are contemplated including, but not limited to, HI-CAP 100 and HI-CAP 200.

The present invention is not limited to any particular percentage of conjugated linoleic acid moiety as compared to the excipient. In some embodiments, the powder is greater than 20% conjugated linoleic acid moiety on a weight/weight basis. In other embodiments, the powder is greater than 35% conjugated linoleic acid moiety on a weight/weight basis. In further embodiments, the powder is greater than 50% conjugated linoleic acid moiety on a weight/weight basis. In further embodiments, the powder is greater than 65% conjugated linoleic acid moiety on a weight/weight basis. In still further embodiments, the powder is between 20% and 65% conjugated linoleic acid moiety on a weight/weight basis. In some embodiments, the powder if free flowing. In other embodiments, the powder is odorless.

In still further embodiments, the present invention provides a composition comprising a foodstuff and the powder described above. The present invention is not limited to any particular foodstuff. Indeed, a variety of foodstuffs are contemplated, including, but not limited to, vegetables, meats, fruits, dairy products, breads, and powders, processed products (e.g., nutrition bars, shakes, etc.), and combinations thereof.

In some embodiments, the present invention provides a composition comprising an excipient and an oil. In preferred embodiments, the composition is greater than 50% oil on a weight/weight basis. In other embodiments, the composition is greater than 60% oil on a weight/weight basis. In still further preferred embodiments, the excipient is selected from HI-CAP 100 and HI-CAP 200. In particularly preferred embodiments, the compositions are free-flowing powders. In other preferred embodiments, the oil comprises a CLA moiety selected from the group consisting of free fatty acids, triglycerides, and alkylesters and combinations therof.

The present invention also provides methods for making free flowing powders comprising providing an excipient and an oil, forming an oil-in-water emulsion with the excipient and oil, and spray drying the emulsion under conditions such that a free flowing powder is formed. The present method is not limited to powder containing any particular oil. Indeed, a the use of a variety of oils is contemplated including, but not limited to, conjugated linoleic acid triglycerides, borage oil, evening primrose oil, flaw oil, and free fatty acid oils such as free fatty acids of conjugated linoleic acid. The present invention is not limited to any particular excipient. Indeed, the use of variety of excipients is contemplated, including, but not limited to, HI-CAP 100 and HI-CAP 200. In some preferred embodiments, the oil and excipient are provided at concentration so that the resulting powder is greater than about 40% oil on a weight/weight basis as compared to the excipient. In still further embodiments, the oil and excipient are provided at concentrations so that the resulting powder is greater than about 50% oil on a weight/weight basis as compared to the excipient. In still other embodiments, the oil and excipient are provided at concentrations so that the resulting powder is greater than about 60% oil on a weight/weight basis as compared to the excipient. In other preferred embodiments, the oil comprises a CLA moiety selected from the group consisting of free fatty acids, triglycerides, and alkylesters and combination therof. In still further embodiments, the present invention provides compositions produced by the previously described method.

DEFINITIONS

As used herein, "conjugated linoleic acid" or "CLA" refers to any conjugated linoleic acid or octadecadienoic free fatty acid. It is intended that this term encompass and indicate all positional and geometric isomers of linoleic acid with two conjugated carbon-carbon double bonds any place in the molecule. CLA differs from ordinary linoleic acid in that ordinary linoleic acid has double bonds at carbon atoms 9 and 12. Examples of CLA include cis- and trans isomers ("E/Z isomers") of the following positional isomers: 2,4-octadecadienoic acid, 4,6-octadecadienoic acid, 6,8-octadecadienoic acid, 7,9-octadecadienoic acid, 8,10-octadecadienoic acid, 9,11-octadecadienoic acid and 10,12 octadecadienoic acid, 11, 13 octadecadienoic acid. As used herein, "CLA" encompasses a single isomer, a selected mixture of two or more isomers, and a non-selected mixture of isomers obtained from natural sources, as well as synthetic and semisynthetic CLA.

As used herein, the term "isomerized conjugated linoleic acid" refers to CLA synthesized by chemical methods (e.g., aqueous alkali isomerization, non-aqueous alkali isomerization, or alkali alcoholate isomerization).

As used herein, the term "conjugated linoleic acid moiety" refers to any compound or plurality of compounds containing conjugated linoleic acids or derivatives. Examples include, but are not limited to fatty acids, alkyl esters, and triglycerides of conjugated linoleic acid.

As used herein, it is intended that "triglycerides" of CLA contain CLA at any or all of three positions (e.g., SN-1, SN-2, or SN-3 positions) on the triglyceride backbone. Accordingly, a triglyceride containing CLA may contain any of the positional and geometric isomers of CLA.

As used herein, it is intended that "esters" of CLA include any and all positional and geometric isomers of CLA bound through an ester linkage to an alcohol or any other chemical group, including, but not limited to physiologically acceptable, naturally occurring alcohols (e.g., methanol, ethanol, propanol). Therefore, an ester of CLA or esterified CLA may contain any of the positional and geometric isomers of CLA.

It is intended that "non-naturally occurring isomers" of CLA include, but are not limited to c11,t13; t11,c13; t11,t13; c11,c13; c8,t10;t8,c10; t8,t10; c8,c10; and trans-trans isomers of octadecadienoic acid, and does not include t10,c12 and c9,t11 isomers of octadecadienoic acid. "Non-naturally occurring isomers" may also be referred to as "minor isomers" of CLA as these isomers are generally produced in low amounts when CLA is synthesized by alkali isomerization.

As used herein, "low impurity" CLA refers to CLA compositions, including free fatty acids, alkylesters, and triglycerides, which contain less than 1% total 8,10 octadecadienoic acids, 11,13 octadecadienoic acids, and trans-trans octadecadienoic acids.

As used herein, "c" encompasses a chemical bond in the cis orientation, and "t" refers to a chemical bond in the trans orientation. If a positional isomer of CLA is designated without a "c" or a "t", then that designation includes all four possible isomers. For example, 10,12 octadecadienoic acid encompasses c10,t12; t10,c12; t10,t12; and c10,c12 octadecadienoic acid, while t10,c12 octadecadienoic acid or CLA refers to just the single isomer.

As used herein, the term "oil" refers to a free flowing liquid containing long chain fatty acids (e.g., CLA), triglycerides, or other long chain hydrocarbon groups. The long chain fatty acids, include, but are not limited to the various isomers of CLA.

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human consumption.

As used herein, the term "foodstuff" refers to any substance fit for human or animal consumption.

As used herein, the term "volatile organic compound" refers to any carbon-containing compound which exists partially or completely in a gaseous state at a given temperature. Volatile organic compounds may be formed from the oxidation of an organic compound (e.g., CLA). Volatile organic compounds include, but are not limited to pentane, hexane, heptane, 2-butenal, ethanol, 3-methyl butanal, 4-methyl pentanone, hexanal, heptanal, 2-pentyl furan, octanal.

As used herein, the term "metal oxidant chelator" refers to any antioxidant that chelates metals. Examples include, but are not limited to lecithin and citric acid esters.

As used herein, the term "alcoholate catalyst" refers to alkali metal compounds of any monohydric alcohol, including, but not limited to, potassium methylate and potassium ethylate.

As used herein, the term "free flowing" refers to the ability of particulate matter to flow without agglomeration of the particles to each other or to other materials.

As used herein, the term "odorless" as used in reference to powders of CLA refers a powder that has the same odor (or lack thereof) as the excipient used to form the powder.

As used herein, the term "powdering agent" refers to a composition (e.g., a starch based composition) used to form powders of oils or other liquids.

DETAILED DESCRIPTION OF THE INVENTION

The present invention relates to the field of human and animal nutrition, and in particular to a novel composition of conjugated linoleic acid (CLA) powder. The CLA powder finds many uses. In particular, the CLA powder may be used for any use that free fatty acids or triglycerides of CLA are normally used. The CLA powder is also more stable to oxidation than compositions consisting only of free fatty acids. Furthermore, the CLA powder has good organoleptic properties. The powder is essentially tasteless and ingestion of the powder does not cause the undesired belching that free fatty acid oils of CLA cause in some individuals.

The CLA powder of the present invention is particularly suited for use in food products and animal feeds. For the purposes of this application, food products containing CLA means any natural, processed, diet or non-diet food product to which CLA has been added. The CLA powder may be directly incorporated into various food products, including, but not limited to diet drinks, diet bars, supplements, prepared frozen meals, candy, snack products (e.g., chips), prepared meat products, milk, cheese, yogurt and any other fat or oil containing foods. In some preferred embodiments, the CLA powder is provided in products formulated for very low calorie diets. It is contemplated that the CLA powder of the present invention is superior in taste and smell to food products containing free fatty acids of CLA. Accordingly, some embodiments of the present invention provide a food product containing CLA powder, wherein the taste and smell of the food product is not affected.

The CLA powder of the present invention may be provided in a variety of forms. In some embodiments, administration is oral. The CLA powder may be further formulated with suitable carriers such as starch, sucrose or lactose in tablets, pills, dragees, and capsules. Preferably, the CLA powder formulations contain antioxidants, including, but not limited to Controx (Grunau (Henkel), Illertissen, Del.), Herbalox (an extract of rosemary; Kalsec, Kalamazoo, Mich.), Covi-OX (Grunau (Henkel), Illertissen, Del.), and oil soluble forms of vitamin C. The CLA may be provided in aqueous solution, oily solution, or in any of the other forms discussed above. The tablet or capsule of the present invention may be coated with an enteric coating which dissolves at a pH of about 6.0 to 7.0. A suitable enteric coating which dissolves in the small intestine but not in the stomach is cellulose acetate phthalate.

The CLA powder of the present invention is formed by combining a CLA moiety (e.g., free fatty acids of CLA, CLA alkylesters, or triglycerides containing CLA) with an excipient or powdering agent. The mixture is then formed into a powder by methods such as spray drying (See, e.g., U.S. Pat. No. 4,232,052, incorporated herein by reference). In general, spray drying involves liquefying or emulsifying a substance and then atomizing it so that all but a small percentage of water is removed, yielding a free flowing powder. Suitable spray drying units include both high pressure nozzle spray driers and spinning disk or centrifugal spray driers. The present inventors have discovered that powders containing high loads (e.g., 40%–65%) conjugated linoleic acid and/or other oils (e.g., evening primrose oil, borage oil, flax oil, CLA oil) can be formed by the simple spray drying of the emulsion of the oil, excipient and water. It is not necessary to incorporate more complex methods involving spraying into a fluidized bed or spraying in a countercurrent fashion.

The present invention is not limited to any particular excipient. Indeed, a variety of excipients are contemplated, including, but not limited to, HI-CAP 100 (National Starch, Bridgewater, N.J.) and HI-CAP 200 (National Starch, Bridgewater, N.J.). The powder of the present invention contains a high percentage of oil as compared to the excipient. In some embodiments, the oil is 20% of the powder on a weight/weight basis (i.e., the powder contains 20 grams of oil for every 100 grams of powder). In other embodiments, the oil is 35% of the powder on weight/weight basis. In still other embodiments, the oil is at least 50% of the powder on a weight/weight basis. In further embodiments, the oil is at least 60%–65% of the powder on a weight/weight basis. In each case, the oil powder is free flowing and odorless. In preferred embodiments, the oil comprises a CLA moiety. In particularly preferred embodiments, the oil comprises CLA fatty acids, CLA triglycerides and/or CLA alkylesters.

In some preferred embodiments, the CLA moiety is a triglyceride containing CLA, as described in Examples 5, 6, and 12. In these embodiments, the triglycerides may be partially or wholly comprised of CLA attached to a glycerol backbone. Preferably, the CLA used in the synthesis of the triacylglycerol is made using alkali alcoholate catalysts under conditions such that isomerized CLA contains less than 1% of 8,10 octadecadienoic acid, 11,13 octadecadienoic acid, and trans-trans octadecadienoic acid. The CLA used to make the triacylgycerols is preferably treated (e.g., by molecular distillation and adsorption) to remove volatile organic compounds to a level of below 100 ppm, preferably below 10 ppm. The pure triacylglycerols highly enriched for CLA (90–96 percent) may be confirmed by H NMR. Esterification proceeds using immobilized Candida antarctica Lipase. Preferably, the CLA will contain at least 40 and upwardly 45–48 percent of c9,t11-octadecadienoic and t10, c12-octadecadie acids, and mixtures thereof.

The immobilized *Candida antarctica* lipase is to be employed in a manner similar to that described for n-3 type polyunsaturated fatty acids. The esterification reaction is conducted at 50°–75° C., preferably 65° C., in the absence of any solvent and a vacuum employed in order to remove the co-produced water or alcohols (from esters) upon formation. This shifts the triacylglycerol production to completion and ensures a highly pure product virtually free of any mono- and diacylglycerols in essentially quantitative yields. Stoichiometric amounts of free fatty acids may be used (i.e., 3 molar equivalents as based on glycerol or 1 molar equivalent as based on number of mol equivalents of hydroxyl groups present in the glycerol moiety). Only 10% dosage of lipase as based on total weight of substrates is needed, which can be used a number of times. This is very important from the productivity point of view. All this, together with the fact that no solvent is required, renders this process a high feasibility from the scaling-up and industrialization point of view, since the cut in volume and bulkiness is enormous. Also, a slight excess of free fatty acids may be used in order to speed up the reaction toward the end and ensure a completion of the reaction.

At the initiation of the reaction, the 1- or 3-monoacylglyeride is formed first, followed by the 1,3 diacylglyeride, and finally the triglyceride at the more extended reaction times. The mono- and diacylglyerides are useful intermediates in that they manifest biological activity, but have greater solubility in aqueous cellular environments and can participate in alternative molecular synthetic pathways such as synthesis of phospholipids or other functional lipids. In contrast, triglycerides are frequently deposited intact in cell membranes or storage vesicles. Thus, the administration of CLA in mono-, di- or triglycerol form rather than free fatty acid or ester, may influence the mode and distribution of uptake, metabolic rate and structural or physiological role of the CLA component.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: M (molar); mM (millimolar); μM (micromolar); kg (kilograms); g (grams); mg (milligrams); μg (micrograms); ng (nanograms); L or l (liters); ml (milliliters); μl (microliters); cm (centimeters); mm (millimeters); nm (nanometers); ° C. (degrees centigrade); KOH (potassium hydroxide); HCL (hydrochloric acid); Hg (mercury).

EXAMPLE 1

Isomerization of Safflower Oil Using Propylene Glycol at Low Temperature

Safflower oil was isomerized in propylene glycol at low temperatures using KOH as a catalyst. The isomerization apparatus consisted of a two-necked flask with a thermometer placed in one neck, leaving a small opening to release excess pressure. A nitrogen supply was attached to the other neck of the flask. Solutions added to the flask were agitated by the use of a magnetic bar and a magnetic stirrer. The temperature of the flask was controlled by placing the flask in a thermostat-controlled oil bath placed on the magnetic stirrer.

The flask was filled with 60.27 g propylene glycol and 28.20 g KOH and immersed into the oil bath. The temperature was increased to 130° C. to dissolve the KOH. After the KOH had dissolved, 60.09 g of safflower oil was introduced into the flask. A high volume of nitrogen was circulated through the two-neck flask for 5 min. and then reduced to a lower volume. The mixture was heated to 150° C., which took approximately 40 min. The mixture was then allowed to react at 150° C. for 3.5 hours. At intervals, 3 ml samples were withdrawn for analysis.

The samples were placed directly into 6 ml of hot water and citric acid was added in excess until the free fatty acids separated out as the top layer. Heating was necessary to prevent solidification while the citric acid was added. To convert the free fatty acids into methylesters for analysis by Gas Chromatography, 0.025 g of the free fatty acids, 5 ml of a 4% solution of HCl and ethanol were added to a test tube. Nitrogen was added to the tube, then the tube was sealed and placed in a water bath at 60° C. for 20 min. The tube was then cooled and 1 ml purified water and 5 ml isooctane were added. Nitrogen was added to the tube and the tube was shaken for 30 seconds. The resulting upper layer was added to 1 μl of purified water in a new test tube and again shaken under nitrogen. The resulting upper layer was then washed of isooctane and decanted into a third test tube. A small amount of sodium sulfate was added for water absorption. A 1 μl sample was then injected directly into the Gas chromatograph.

The gas chromatography conditions were as follows:

| | |
|---|---|
| System: | Perkins-Elmer Auto System |
| Injector: | Splitless at 240° C. |

-continued

| | |
|---|---|
| Detector: | Flame Ionization Detector at 280° C. |
| Carrier: | Helium |
| Column: | WCOT Fused Silica 0.25 mm X100M, CP-SL 88 for FAME, DF 0.2 |
| Oven Program: | 80° C. (0 mm.) increasing to 220° C. at 10° C. per min. and held at 220° C. for 10 mm. |

All results are expressed as the relative peak area percentage. Standards are generally unavailable, so the peaks which eluted were verified with other systems. GC-MS determines the number, but not the position of cis and trans bonds. Therefore, NMR analysis was used to verify the bond positions. The main peaks were c9,t11 and t10,c12. For NMR analysis of CLA isomers, please see Marcel S. F. Lie Ken Jie and J. Mustafa, *Lipids*, 32 (10) 1019–34 (1997), incorporated herein by reference.

This data, presented in Table 1 and summarized in Table 5, demonstrates that isomerization of safflower oil using polypropylene glycol as a solvent, KOH as a catalyst, and low temperatures results in the production of conjugated linoleic acid lacking 8,10 and 11,13 isomers. The highly polar columns utilized in this experiment may be successfully used to separate the 8,10 and 11,13 isomers from c9,t11 and t10,c12 isomers. The 8,10 isomers tend to coelute or elute just after the c9,t11 isomer. The 11,13 isomer elutes in front of the t10,c11 isomer or coelutes with the t10,c12 isomer, depending on the column conditions.

The conjugated linoleic acid produced according to this method by characterized by comparing the various isomers produced. First, the isomerization reaction went essentially to completion. The completeness of the reaction is obtained by dividing the total peak area the for linoleic acid isomers minus residual c9, t12 linoleic acid by the total peak area. This value is 0.994. Second, the ratio of c9,t11 and t10,c12 isomers to total peak area may be determined. This value is 0.953. Third, the ratio of the t9,t11 and t10,t12 isomers to the c9,t11 and t10,c12 isomers may be determined. This value is 0.010. Fourth, the ratio of the t9,t11 and t10,t12 isomers to total peak area may be determined. This value is 0.009. Fifth, the ratio of the t10,c12 isomer to the c9,t11 isomer may be determined. This value is 1.018. These ratios are summarized in Table 11.

EXAMPLE 2

Aqueous Isomerization at High Temperature and Pressure

Fifty grams of water and 25.32 g NaOH were added to a high pressure reactor (Parr Model 450 ML Benchtop Alloy 400, equipped with a pressure gauge and stirrer.) The NaOH was allowed to dissolve and 94.0 g safflower oil was added to the reactor. The reactor was closed and flushed for 2 min. with nitrogen and then all valves were closed. The reactor was heated in an electrical gasket to 210° C. and maintained at that temperature for 6 hours. The temperature was then reduced to 60° C. before pressure was released and the reactor opened. Two grams of the resulting solidified soap were taken from the reactor and dissolved in water at approximately 40° C. Citric acid was then added to reduce the pH of the solution to below 6. A sample was withdrawn from the fatty acid top layer and prepared for Gas Chromatography as in Example 1.

The results of the gas chromatography are presented in Table 2 and summarized in Table 5. These data indicate that this isomerization method results in the formation of relatively high amounts of the 8,10 and 11,13 isomers. Ratios are presented in Table 6.

EXAMPLE 3

Non-aqueous Alkali Isomerization of Safflower Oil at High Temperature and Pressure Propylene glycol (100.48 g) and 46.75 g of KOH were added to a high-pressure reactor as described in Example 2. The reactor was then heated to 130° C. to dissolve the KOH, 100.12 g of safflower oil were then added to the KOH-propylene glycol mixture. The reactor was closed, flushed for 1 min. with nitrogen, and all valves closed. The reactor was then heated to 210° C. and maintained at that temperature for 1 hour. The reactor was cooled and the contents decanted into 120 g of hot water. While stirring, 35.3 g 37% HCl and 27.59 g citric acid were serially added to the fatty acids. A sample was taken from the top layer and dried in a vacuum flask at 60° C. A sample of the resulting fatty acids was analyzed by gas chromatography as described in Example 1.

The results are presented in Table 3 and summarized in Table 5. This experiment demonstrates that isomerization of safflower oil with KOH and a non-aqueous solvent at high temperature results in the formation of significant amounts of 8,10 and 11,13 isomers, as well as t9,t11 and t10,t12 isomers. Ratios are presented in Table 6.

EXAMPLE 4

Aqueous Alkali Reaction at Low Temperature

Water (49.94 g) and 39.96 g NaOH were added to a high-pressure reactor as described in Example 3. This mixture was heated until the NaOH dissolved. Next, 100.54 g of safflower oil was added to the high-pressure reactor, the reactor was flushed with nitrogen, and all valves closed. The high-pressure reactor was heated to 179° C. for 22.5 hours. Samples were prepared for Gas Chromatography as in Example 3. The data is provided in Table 4 and summarized in Table 5. This experiment demonstrates that when low temperatures are used for aqueous alkali isomerization, the conjugation reaction does not go to completion. Furthermore, significant amounts of the 8,10 and 11,13 isomers are produced. Ratios are presented in Table 6.

TABLE 1

| Peak # | Time (Min) | Component Name | Area (%) | Area ($\mu V \cdot s$) | Height ($\mu V$) |
|---|---|---|---|---|---|
| 1 | 38.164 | | 0.08 | 4101.65 | 622.28 |
| 2 | 49.539 | C16:0 | 6.29 | 335897.80 | 32745.95 |
| 3 | 53.107 | C16:1 | 0.06 | 3240.60 | 447.82 |
| 4 | 61.620 | C18:0 | 2.38 | 127182.30 | 12999.14 |
| 5 | 64.821 | C18:1 c9 | 12.34 | 659111.72 | 52209.40 |
| 6 | 65.254 | | 0.57 | 30402.68 | 3475.09 |
| 7 | 67.263 | | 0.11 | 5757.35 | 758.08 |
| 8 | 67.940 | | 0.10 | 5523.00 | 700.44 |
| 9 | 68.755 | | 0.24 | 12816.90 | 1543.27 |
| 10 | 69.310 | | 0.22 | 11803.80 | 1430.59 |
| 11 | 69.846 | C18:2 c9,c12 | 0.44 | 23336.75 | 2500.24 |
| 12 | 73.618 | | 0.28 | 14828.70 | 1838.66 |
| 13 | 76.621 | | 0.16 | 8400.65 | 1050.19 |
| 14 | 77.388 | CLA c9,t11 | 36.51 | 1950669.98 | 124313.83 |
| 15 | 78.370 | CLA t10,c12 | 37.16 | 1985488.96 | 132265.33 |
| 16 | 78.664 | CLA c9,c11 | 1.06 | 56583.10 | 5699.43 |
| 17 | 78.880 | CLA c10,c12 | 1.26 | 67503.55 | 4572.65 |

TABLE 1-continued

| Peak # | Time (Min) | Component Name | Area (%) | Area (μV · s) | Height (μV) |
|---|---|---|---|---|---|
| 18 | 80.102 | CLA t9,t11/t10,t12 | 0.73 | 39110.00 | 4743.28 |
| 19 | 85.165 | | 0.03 | 1621.65 | 231.32 |
| | | | 100.00 | 5343381.15 | 384147.01 |

TABLE 2

| Peak # | Time (Min) | Component Name | Area (%) | Area (μV · s) | Height (μV) |
|---|---|---|---|---|---|
| 1 | 36.554 | | 0.09 | 4122.05 | 627.02 |
| 2 | 47.785 | C16:0 | 6.68 | 290571.30 | 28224.34 |
| 3 | 51.280 | C16:1 | 0.07 | 3188.05 | 425.57 |
| 4 | 59.787 | C18:0 | 2.63 | 114362.95 | 12678.63 |
| 5 | 62.923 | C18:1 c9 | 13.12 | 570712.08 | 42259.71 |
| 6 | 63.346 | | 0.72 | 31329.22 | 3774.35 |
| 7 | 65.355 | | 0.54 | 23620.70 | 2848.35 |
| 8 | 66.034 | | 0.67 | 28980.78 | 3333.95 |
| 9 | 66.574 | | 0.10 | 4370.91 | 594.22 |
| 10 | 66.811 | | 0.35 | 15045.61 | 1469.30 |
| 11 | 67.352 | | 0.41 | 18002.20 | 2035.78 |
| 12 | 67.889 | C18:2 c9,c12 | 1.43 | 62002.15 | 6714.22 |
| 13 | 69.200 | | 0.09 | 3840.85 | 474.10 |
| | | | | | 474.10 |
| 14 | 71.680 | | 0.30 | 13099.10 | 1744.21 |
| 15 | 74.640 | | 1.62 | 70689.87 | 4117.23 |
| 16 | 75.310 | CLA c9,t11/8,10 | 24.87 | 1082087.96 | 57619.24 |
| 17 | 76.032 | CLA 11,13 | 14.72 | 640440.14 | 42975.86 |
| 18 | 76.277 | CLA t10,c12 | 16.00 | 695923.85 | 63512.81 |
| 19 | 76.450 | CLA c8,c10 | 1.26 | 54676.10 | 7614.29 |
| 20 | 76.626 | CLA c9,c11 | 2.08 | 90411.44 | 10891.36 |
| 21 | 76.881 | CLA c10,c12 | 3.00 | 130593.96 | 11727.80 |
| 22 | 77.022 | CLA c11,c13 | 1.77 | 77065.69 | 9906.74 |
| 23 | 77.477 | | 0.66 | 28867.85 | 3322.69 |
| 24 | 77.868 | | 0.63 | 27391.94 | 2934.68 |
| 25 | 78.173 | CLA t9,t11/t10,t12 | 6.00 | 260985.40 | 26124.10 |
| 26 | 83.140 | | 0.12 | 5164.40 | 586.21 |
| 27 | 85.878 | | 0.06 | 2735.80 | 347.01 |
| | | | 100.00 | 4350282.35 | 348883.46 |

TABLE 3

| Peak # | Time (Min) | Component Name | Area (%) | Area (μV · s) | Height (μV) |
|---|---|---|---|---|---|
| 1 | 38.249 | | 0.08 | 3999.70 | 599.26 |
| 2 | 49.639 | C16:0 | 6.41 | 333807.80 | 32279.13 |
| 3 | 53.218 | C16:1 | 0.06 | 3123.00 | 427.39 |
| 4 | 55.508 | | 0.03 | 1322.20 | 190.60 |
| 5 | 61.753 | C18:0 | 2.55 | 132854.50 | 14939.09 |
| 6 | 64.104 | C18:1 c9 | 0.03 | 1640.30 | 245.73 |
| 7 | 64.950 | | 12.92 | 672672.91 | 53345.47 |
| 8 | 65.382 | | 0.64 | 33297.29 | 3728.28 |
| 9 | 65.783 | | 0.03 | 1411.20 | 219.76 |
| 10 | 67.403 | | 0.62 | 32194.66 | 2836.09 |
| 11 | 67.793 | | 0.24 | 12660.05 | 1495.10 |
| 12 | 68.088 | | 0.68 | 35371.43 | 3210.82 |
| 13 | 68.421 | | 0.07 | 3684.10 | 473.77 |
| 14 | 68.635 | | 0.04 | 1948.63 | 257.65 |
| 15 | 68.890 | | 0.29 | 14979.18 | 1499.63 |
| 16 | 69.192 | | 0.04 | 2268.69 | 324.39 |
| 17 | 69.430 | | 0.25 | 13028.21 | 1369.93 |
| 18 | 69.947 | C18:2 c9,c12 | 0.23 | 11895.70 | 1125.77 |
| 19 | 70.341 | | 0.02 | 1168.20 | 196.75 |
| 20 | 73.741 | | 0.31 | 15930.60 | 1965.82 |
| 21 | 75.448 | | 0.08 | 3906.00 | 387.98 |
| 22 | 76.768 | | 1.79 | 93172.74 | 6637.34 |
| 23 | 77.002 | | 0.63 | 32882.76 | 5024.06 |

TABLE 3-continued

| Peak # | Time (Min) | Component Name | Area (%) | Area (μV · s) | Height (μV) |
|---|---|---|---|---|---|
| 24 | 77.389 | CLA c9,t11/8,10 | 15.62 | 813447.45 | 57234.62 |
| 25 | 77.735 | | 1.92 | 99754.50 | 8641.88 |
| 26 | 78.045 | CLA 11,13 | 4.03 | 209728.35 | 19826.20 |
| 27 | 78.335 | CLA t10,c12 | 12.63 | 657681.44 | 62016.93 |
| 28 | 78.566 | CLA c8,c10 | 0.64 | 33432.80 | 5277.06 |
| 29 | 78.727 | CLA c9,c11 | 2.21 | 114935.49 | 10791.54 |
| 30 | 79.079 | CLA c10,c12 | 3.98 | 207339.28 | 12766.61 |
| 31 | 79.663 | CLA c11,c13 | 1.40 | 73036.34 | 6275.58 |
| 32 | 80.516 | CLA t9,t11/t10,t12 | 29.39 | 1529956.09 | 100323.85 |
| 33 | 82.318 | | 0.03 | 1563.70 | 230.42 |
| 34 | 85.289 | | 0.07 | 3657.50 | 423.53 |
| 35 | 88.093 | | 0.05 | 2368.50 | 301.03 |
| | | | 100.00 | 5206121.30 | 416889.05 |

TABLE 4

| Peak # | Time (Min) | Component Name | Area (%) | Area (μV · s) | Height (μV) |
|---|---|---|---|---|---|
| 1 | 38.154 | | 0.09 | 3371.70 | 501.86 |
| 2 | 49.501 | C16:0 | 6.80 | 253221.00 | 25807.11 |
| 3 | 53.100 | C16:1 | 0.07 | 2723.55 | 353.01 |
| 4 | 55.391 | | 0.03 | 1078.10 | 142.65 |
| 5 | 61.618 | C18:0 | 2.68 | 100015.20 | 11002.94 |
| 6 | 63.990 | | 0.03 | 946.40 | 156.50 |
| 7 | 64.791 | C18:1 c9 | 13.13 | 489016.55 | 38313.02 |
| 8 | 65.270 | | 0.69 | 25645.55 | 2670.46 |
| 9 | 67.296 | | 0.12 | 4466.65 | 558.35 |
| 10 | 67.960 | | 0.11 | 4012.70 | 517.76 |
| 11 | 68.800 | | 0.37 | 13840.49 | 1314.91 |
| 12 | 69.370 | | 0.30 | 11141.11 | 1245.85 |
| 13 | 70.001 | C18:2 c9,c12 | 20.52 | 764287.35 | 62474.10319.72 |
| 14 | 73.538 | | 0.30 | 11075.20 | 1357.19 |
| 15 | 76.519 | | 0.42 | 15662.14 | 1154.22 |
| 16 | 77.231 | CLA c9,t11/8,10 | 22.45 | 836230.58 | 56972.76 |
| 17 | 77.911 | CLA 11,13 | 7.56 | 281633.54 | 24467.27 |
| 18 | 78.197 | CLA t10,c12 | 19.77 | 736384.86 | 66688.46 |
| 19 | 78.559 | CLA c8,c10 | 1.21 | 45158.40 | 3837.29 |
| 20 | 78.787 | CLA c9,c11 | 0.87 | 32564.06 | 3409.07 |
| 21 | 78.953 | CLA c10,c12 | 0.89 | 33053.57 | 2499.70 |
| 22 | 79.413 | CLA c11,c13 | 0.12 | 4453.10 | 353.06 |
| 23 | 79.792 | | 0.13 | 4936.60 | 436.59 |
| 24 | 80.052 | CLA t9,t11/t10,t12 | 1.13 | 42203.55 | 4550.59 |
| 25 | 82.298 | | 0.03 | 981.60 | 150.46 |
| 26 | 82.946 | | 0.03 | 1107.95 | 151.48 |
| 27 | 85.135 | | 0.10 | 3639.90 | 383.36 |
| 28 | 87.927 | | 0.06 | 2212.50 | 254.61 |
| | | | 100.00 | 3725063.90 | 311570.23 |

TABLE 5

Relative Area Percentage

| Isomer | Example 1 | Example 2 | Example 3 | Example 4 |
|---|---|---|---|---|
| c9,t12 | 0.44 | 1.43 | 0.23 | 20.52 |
| c9,t11 | 36.51 | na | na | na |
| c9,t11/8,10 | <0.5* | 24.87 | 15.62 | 22.45 |
| t10,c12 | 37.16 | 16.00 | 12.63 | 19.77 |
| c9,c11 | 1.06 | 2.08 | 2.21 | 0.87 |
| c8,c10 | <0.5 | 1.26 | 0.64 | 1.21 |
| c10,c12 | 1.26 | 3.00 | 3.98 | 0.89 |
| t9,t11/t10,t12 | 0.73 | 6.00 | 29.39 | 1.13 |

TABLE 5-continued

| | Relative Area Percentage | | | |
|---|---|---|---|---|
| Isomer | Example 1 | Example 2 | Example 3 | Example 4 |
| 11,13 | <0.5 | 10.23 | 4.05 | 7.65 |
| c11,c13 | <0.5 | 1.77 | 1.40 | 0.12 |
| Unidentified | <0.5 | 2.91 | 4.34 | 0.55 |
| CLA Total | 76.88 | 72.61 | 74.24 | 54.55 |
| Total area | 77.32 | 74.04 | 74.47 | 75.07 |

*total percentage of 8,10 is less than 0.5
na - value is reflected as component of c9,t11/8,10

TABLE 6

| Isomer Ratio | | Example 1 | Example 2 | Example 3 | Example 4 |
|---|---|---|---|---|---|
| Total CLA isomer | Total peak area | 0.994 | 0.981 | 0.997 | 0.727 |
| c9,t11-t10,c12 | Total peak area | 0.953 | 0.552* | 0.379* | 0.562* |
| t9,t11-t10,t12 | c9,t12-t10,c12 | 0.010 | 0.147* | 1.040* | 0.027* |
| t9,t11-t10,t12 | Total peak area | 0.009 | 0.081 | 0.395 | 0.015 |
| Total 11,13 | Total peak area | na | 0.223 | 0.073 | 0.102 |
| t10,c12 | c9,t11 | 1.018 | 1.554* | 0.809* | 0.881* |

*c9,t11 includes 8,10 isomer
na - no 11,13 detected

EXAMPLE 5

The Preparation of Triacylglycerols of CLA by Direct Esterification

General. H nuclear magnetic resonance spectra were recorded on a Bruker AC 250 NMR spectrometer in deuterated chloroform as a solvent. HPLC separations were carried out by a PrepLC™ System 500A instrument from Waters using the PrepPak® 500/Silica Cartridge column from Millipore, eluting with 10% diethyl ether in petroleum ether. Analytical GLC was conducted on a Perkin-Elmer 8140 Gas Chromatograph according to a previously described procedure, as described in Haraldsson, et al., Acta Chem Scanned 45: 723 (1991).

The immobilized *Candida antarctica* lipase was provided by Novo Nordisk in Denmark as Novozyme™. It was used directly as provided in the esterification experiments. Analytical grade diethyl ether purchased from Merck was used without any purification, but synthetic grade n-hexane also from Merck was freshly distilled prior to use in extractions and HPLC chromatography. Glycerol (99%) was purchased from Sigma and Aldrich Chemical Company and used without further purification. The CLA concentrate was provided by Natural Lipids in Norway as free fatty acids as Tonalin™. Its purity was confirmed by analytical GLC and high-field NMR spectroscopy which revealed some glyceride impurities. The CLA concentrate was found to contain 43.3% 9-cis,11-trans-linoleic acid, 44.5% 10-trans, 12-cis-linoleic acid, 5.4% of other CLA isomers, 5.6% oleic acid and 0.6% each of palmitic and stearic acid as determined by GLC at the Science Institute.

EXAMPLE 6

The Preparation of Triacylglycerols of CLA by Direct Esterification

Immobilized *Candida antarctica* lipase (1.25 g) was added to a mixture of glycerol (1.22 g. 13.3 mmol) and CLA as free fatty acid (M. wt. 280.3 g/mol; 11.6 g, 41.5 mmol). The mixture was gently stirred on a magnetic stirrer hot plate at 65° C. under continuous vacuum of 0.01–0.5 Torr. The volatile water produced during the progress of the reaction was continuously condensed into liquid nitrogen cooled traps. After 48 h the reaction was discontinued, n-hexane added and the enzyme separated off by filtration. The organic phase was treated with an alkaline aqueous solution of sodium carbonate to remove excessive free fatty acids (when required). The organic solvent (after drying over anhydrous magnesium sulfate when appropriate) was removed in vacuo on a rotary evaporator followed by high-vacuum treatment to afford the virtually pure product as a slightly yellowish oil (10.9 g; average M. wt. 878.6 g/mol; 93% yield). When stoichiometric amounts of free fatty acids were used, titration by standardized sodium hydroxide was applied to determine the free fatty acid content of the crude reaction product (less than 1% free fatty acid content as based on number of mol of ester groups, corresponding to at least 99% incorporation, which is equivalent to the minimum of 97% triglyceride content). The crude product was directly introduced into HPCL eluting with 10% diethylether in n-hexane to afford 100% pure triglyceride as a colourless oil. 250 MHz 1H NMR (CDCl3) δ (ppm) 6.35–6.23 (3H, ddt, Jtrans=15.0 Hz, J=10.9 Hz, Jallyl=1.3,=CHCH=CH), 5.98–5.90 (3H, dd, Icis=10.9, J=10.9, —CH=CHCH=), 5.71–5.59 (3H, dtd, Jtrans=15.0 Hz, J=6.9 Hz, J=6.9 Hz, J=2.2 Hz, =CH=CHCH2—), 5.35–5.26 (4H, m, =CH2CH=CH— and —CH2C —ICH2—), 4.33–4.26 (2H, dd, Jgem=11.9 Hz, J=4.3, —CH2CHCH2—), 4.18–4.10 2H, dd, Jgem=1.8 Hz, J=6.0, —CH2CHCH2—), 2.37–2.31 (6H, t, J=7.4 H2, —CH2COOR), 2.19–2.05 (12H, m, —CH2CH=CH—), 1.66–1.60 (6H, qu., J=Hz, —CH2CH2COOR), 1.43–1.30 (18H, m, —CH2—), 0.91–0.86 (9H, t, J=6.7 Hz, —CH3). 13C—NMR (CDCl3): δ (ppm) 173.2, 172.8, 134.6, 130.0, 128.6, 125.5, 68.8, 62.0, 34.0, 32.9, 31.6, 29.6–28.9 (6C), 27.6, 24.8, 22.5, 14.1.

In order to monitor the progress of the reaction and provide more details about the composition of individual glycerides during the reaction, samples were collected regularly as the reaction proceeded. They were analyzed by HNMR spectroscopy and provided a good insight into the composition of mono-, di- and triacylglycerols during the progress of the reaction. The results are demonstrated in Table 7 below. As can be noticed from the table, 1,3-diacylglycerols dominated the reaction mixture during the first two hours of the reaction. After 4 hours triacylglycerols took over and had reached 98% composition after 22 hours and 100% after 48 hours. As would be expected 1,2-diacylglycerols reached considerably lower levels than the 1,3-diacylglycerols. 1-monoacylglycerols reached a maximum during the first hour of the reaction, but 2-monoacylglycerols were not detected throughout the reaction.

TABLE 7

| Time | % Incorporation | | | | Residual FFA |
|---|---|---|---|---|---|
| h | 1-MG | 1,2-DG | 1,3-DG | TG | % |
| 0 | 0 | 0 | 0 | 0 | 100 |
| 1 | 8.3 | 15.2 | 39.4 | 7.8 | 29.3 |
| 2 | 2.7 | 9.3 | 46.5 | 17.4 | 24.1 |
| 4 | 1.7 | 7.9 | 25.4 | 49.4 | 15.5 |
| 6 | 0.5 | 5.2 | 16.0 | 68.1 | 10.1 |

TABLE 7-continued

| Time | % Incorporation | | | | Residual FFA |
|---|---|---|---|---|---|
| h | 1-MG | 1,2-DG | 1,3-DG | TG | % |
| 8 | 0.0 | 3.9 | 9.9 | 80.5 | 5.7 |
| 10 | 0.0 | 3.0 | 7.0 | 85.8 | 4.2 |
| 12 | 0.0 | 2.7 | 5.6 | 89.2 | 2.5 |
| 22 | 0.0 | 1.0 | 1.4 | 95.8 | 1.8 |
| 48 | 0.0 | 0.0 | 0.0 | 100 | 0.0 |

EXAMPLE 7

Effect of Varying Temperature and Reaction Duration on CLA Yield and Composition The effect of temperature and reaction duration on the conjugation of safflower oil was determined. Water and NaOH were added to a high pressure reactor (Parr Model 450 ML Benchtop Alloy 400, equipped with a pressure gauge and stirrer) as indicated in Table 1, columns 1 and 2. The NaOH was allowed to dissolve and safflower oil (column 3) was added to the reactor. The reactor was closed and flushed for 2 min. with nitrogen and then all valves were closed. The reactor was heated in an electrical gasket to the desired temperature (column 4) and maintained at that temperature for the desired time (column 5). The temperature was then reduced to 60° C. before pressure was released and the reactor opened. For each reaction, two grams of the resulting solidified soap were taken from the reactor and dissolved in water at approximately 40° C. Citric acid was then added to reduce the pH of the solution to below 6. A sample was withdrawn from the fatty acid top layer and prepared for Gas Chromatography.

The results of the gas chromatography are presented in column 6(total percentage of 9,11 and 10,12 isomers), column 7 (total percentage of 11,13 isomers), and column 8(total percentage of all CLA isomers or yield). These data indicate that as reaction duration and temperature increase, the total amount of conjugation and the percentage of 11,13 isomers increase. Under conditions where formation of the 11,13 isomer is low, the total amount of conjugation is also low.

TABLE 8

| Water gram | NaOH gram | Safflower Oil gram | Mean t. °C. of reaction | Time hours | 9, 11 + 10, 12 area % | 11, 13 area % | CLA total area % |
|---|---|---|---|---|---|---|---|
| 50.21 | 29.93 | 99.94 | 189 | 6.36 | 45.99 | 5.73 | 55.86 |
| 70.20 | 29.93 | 99.94 | 187 | 6.40 | 44.94 | 3.23 | 51.28 |
| 50.10 | 30.17 | 100.74 | 183 | 6.39 | 40.23 | 3.37 | 48.07 |
| 49.91 | 29.93 | 100.40 | 179 | 6.52 | 32.00 | 1.48 | 34.92 |
| 49.97 | 29.80 | 100.02 | 179 | 10.08 | 41.86 | 3.12 | 48.21 |
| 49.94 | 39.84 | 99.84 | 179 | 6.30 | 32.6 | 3.04 | 37.12 |
| 29.50 | 24.83 | 99.21 | 240 | 3.25 | 28.37 | 10.78 | 71.58 |
| 30.33 | 25.15 | 100.43 | 221 | 2.30 | 40.87 | 14.72 | 72.61 |
| 49.92 | 30.00 | 100.36 | 150 | 6.34 | 7.07 | 0 | 7.44 |

EXAMPLE 8

Conjugation of Safflower Fatty Acid Methylester (FAME)

The reaction was carried out in a closed vessel. The following components were mixed together: 100 g safflower FAME and a mixture of approximately 2.8 g KOCH$_3$ and 2.8 g methanol. There was probably more KOMe than methanol due to evaporation of methanol during mixing of the two components. The mixture was stirred for 5 hours at 111–115 deg C. in nitrogen atmosphere in a closed reaction vessel. The distribution of isomers was analyzed by Gas Chromatography. The results are summarized in Table 2. The raw GC data is presented in Table 9. These data indicate that the conjugation safflower FAME may be accomplished under mild conditions, resulting in a product lacking appreciable amounts of undesirable 8,10 and 11,13 isomers.

TABLE 9

| Isomer Distribution | |
|---|---|
| Palmitic acid | 6.6% |
| Stearic acid | 2.7% |
| Oleic acid | 12.9% |
| Linoleic acid | 5.7% (unconjugated) |
| CLA c9,t11 | 34.1% |
| CLA t10,c12 | 33.3% |
| CLA c,c | 1.8% |
| CLA t,t | 1.0% |
| CLA total | 70.2% |

EXAMPLE 9

Large Scale Batch Production of Conjugated Safflower FAME

The production of safflower conjugated FAME may be divided into two steps, methanolysis and conjugation. For methanolysis, 6,000 kg safflower oil was drawn into a closed reactor. The reactor was purged with nitrogen at atmospheric pressure, and 1150 liters of methanol and 160 kg of NaOCH$_3$ (30% solution) were added. The mixture is heated to 65° C. while stirring, and reacted at 65° C. for 2 hours. The resulting bottom layer was decanted while the reactor was purged with nitrogen gas. 1000 liters of water (40–50° C., into which 50 kg citric acid monohydrate has been dissolved) was then added while stirring. The layers were allowed to separate (approx. 60 min.) and the bottom layer decanted while purging the reactor with nitrogen gas. The resulting safflower FAME product was dried at 80° C. under vacuum for one hour.

To conjugate the safflower FAME, 250 kg of KOCH$_3$ dissolved in methanol to form a paste was added to the reactor. The mixture was then heated to 120° C. while stirring and the reaction allowed to continue for 3 hours. The mixture was cooled to 100° C., and 1000 liters of water (40–50° C., into which 50 kg citric acid monohydrate has been dissolved) was added while stirring. The mixture was stirred for 15 minutes and then the layers were allowed to separate for 20 minutes. The bottom layer was decanted and the product dried at 80° C. for 1 hour and then stored under nitrogen.

The resulting CLA was analyzed using a Perkin Elmer Autosystem XL GC under the following conditions:

| Column: | WCOT Fused Silica 100 m × 0.25 mm, Coating CP SIL 88 |
|---|---|
| Carrier: | He gas, 30.0 PSI |
| Temp: | 220 C. |
| Run time: | 35–90 min. |
| Inject.: | Splitless, 240 C. |
| Detect.: | FID, 280 C. |

The GC results are summarized in Tables 10.

TABLE 10

| Peak # | Time (min) | Component Name | Area (%) | Area (μVs) | Height (μV) |
|---|---|---|---|---|---|
| 1 | 46.874 | C16:0 | 6.37 | 29874.50 | 4026.29 |
| 2 | 58.685 | C18:0 | 2.61 | 12231.70 | 1542.34 |
| 3 | 62.141 | C18:1 c9 | 13.14 | 61668.78 | 7369.08 |
| 4 | 62.652 | | 0.70 | 3263.62 | 391.92 |
| 5 | 66.404 | | 0.35 | 1627.60 | 177.41 |
| 6 | 66.917 | | 0.26 | 1239.15 | 157.35 |
| 7 | 67.583 | C18:2 c9,c12 | 5.75 | 26964.95 | 3153.80 |
| 8 | 70.631 | | 0.25 | 1171.90 | 141.41 |
| 9 | 75.011 | CLA c9,t11 | 34.42 | 161529.90 | 17544.79 |
| 10 | 75.936 | CLA t10,c12 | 33.48 | 157129.82 | 17157.21 |
| 11 | 76.400 | CLA c9,c11 | 0.84 | 3935.70 | 302.61 |
| 12 | 76.631 | CLA c10,c12 | 0.49 | 2316.98 | 279.31 |
| 13 | 77.905 | CLA t,t 9,11+ 10,12 | 1.35 | 6344.50 | 710.88 |
| | | | 100.00 | 469299.10 | 52954.41 |

EXAMPLE 10

The following are examples of typical animal rations containing the CLA free fatty acids, triglycerides, and esters of the present invention.

A. Pig Starter Rations

TABLE 11

| Ingredients | lbs. | kgs. |
|---|---|---|
| Corn, yellow (8.4% protein) | 1067 | 484.7 |
| Soy bean meal, solvent extracted, dehulled (47% protein) | 570 | 259 |
| CLA Powder | 5 | 2.3 |
| Whey, dried (12.0% protein) | 300 | 136 |
| Dicalcium phosphate | 24 | 11 |
| Limestone | 16 | 7 |
| Iodized salt | 5 | 2 |
| Trace mineral premix | 5 | 2 |
| Vitamin premix | 8 | 4 |
| Totals | 2000 | 908 |

B. Grower-Finisher Rations For Pigs (From 40–240LBS [18–109KGS])

TABLE 12

| Ingredients | lbs. | kgs. |
|---|---|---|
| Corn, yellow (8.4% protein) | 1566 | |
| Soybean meal, solvent extracted (44% protein) | 380 | |
| CLA Powder | 5 | |
| Dicalcium phosphate | 21 | |
| Limestone | 15 | |
| Iodized Salt | 5 | |
| Trace Mineral Premix | 3 | |
| Vitamin Premix | 3 | |
| Total | 2000 | |

C. Pig Grower Finisher Rations (For Pigs 121–240LBS [55–109KGS])

TABLE 13

| Ingredients | lbs. | kgs. |
|---|---|---|
| Corn, yellow (8.4% protein) | 1687 | |
| Soybean meal, solvent extracted (44% protein) | 265 | |
| CLA Powder | 5 | |
| Dicalcium phosphate | 18 | |
| Limestone | 15 | |
| Iodized salt | 5 | |
| Trace mineral premix | 2 | |
| Vitamin Premix | 3 | |
| Total | 2000 | |

Composition and Analysis of Pig Trace Mineral Remix

TABLE 14

| Element | Source | Amount (lbs) |
|---|---|---|
| Copper (Co) | Copper Sulfate | 1.500 |
| Iodine (I) | Potassium Iodide | 0.010 |
| Iron (Fe) | Ferrous Sulfate | 25.000 |
| Manganese (Mn) | Manganese Sulfate | 2.500 |
| Selenium (Se) | Sodium Selemite) | 0.025 |
| Zinc (Zn) | Zinc Sulfate | 25.000 |
| | Carrier | 45.965 |
| Total | | 100.000 |

Composition of Pig Vitamin Premix

TABLE 15

| Vitamins | Amount |
|---|---|
| Essential | |
| Vitamin A (million IU) | 5.0 |
| Vitamin D (million IU) | 0.6 |
| Vitamin E (thousand IU) | 26.0 |
| Niacin (g) | 25.0 |
| d-Pantothenic acid (g) | 20.0 |
| Riboflavin (g) | 6.0 |
| Vitamin B-12 (mg) | 25.0 |
| Optional | |
| Biotin (g) | 0.3 |
| Menadione (g) | 4.0 |
| Carrier | to 10 lbs |
| Total | 10.0 |

D. 18% Protein Layer Rations for Hens

TABLE 16

| Ingredients | lbs. | kgs. |
|---|---|---|
| Ground yellow corn | 1242 | 564.5 |
| CLA Powder | 5 | 2.3 |
| Alfalfa meal, 17% | 25 | 11.3 |
| Soybean meal, dehulled | 451.6 | 205.3 |
| Meat and bone meal (47%) | 50 | 23.0 |
| DL-methionine | 1.0 | .5 |
| Dicalcium phosphate | 7 | 3.1 |

TABLE 16-continued

|  | lbs. | kgs. |
|---|---|---|
| Ground limestone | 174 | 79.1 |
| Iodized salt | 7 | 3.1 |
| Stabilized yellow grease | 37 | 17.2 |
| Total |  | 909.4 |
| Mineral and vitamin supplements |  |  |
| Calcium pantothenate (mg) |  | 5,000 |
| Manganese (g) |  | 52 |
| Selenium (mg) |  | 90.8 |
| Zinc (g) |  | 16 |
| Vitamin A (IU) |  | 6,000,000 |
| Vitamin $D_3$ (IU) |  | 2,000,000 |
| Choline (mg) |  | 274,000 |
| Niacin (mg) |  | 12,000 |
| Riboflavin (mg) |  | 2,000 |
| Vitamin B-12 |  | 6 |
| Total |  | 2000 |

E. Starter and Finisher Rations for Broilers

TABLE 17

|  | Starter (up to 24 days) | | Finisher (25 days to market) | |
|---|---|---|---|---|
|  | lbs. | kgs. | lbs. | kgs. |
| Ingredients |  |  |  |  |
| Ground yellow corn | 1,106 | 503 | 1235 | 561 |
| CLA Powder | 5 | 2.3 | 5 | 2.3 |
| Soybean meal, dehulled | 605 | 275 | 420 | 191 |
| Alfalfa meal, 17% | — | — | 25 | 11 |
| Corn gluten meal, 60% | 50 | 23 | 75 | 34 |
| Fish meal, herring, 65% | 50 | 23 | 50 | 23 |
| Meat and bone meal, 47% | 50 | 23 | 50 | 23 |
| Dicalcium phosphate | 10 | 4 | 9 | 4 |
| Ground limestone | 16 | 7 | 14 | 6.3 |
| DL-methionine | 0.8 | 0.3 | — | — |
| Stabilized yellow grease | 101 | 45.7 | 110 | 49.4 |
| Iodized salt | 7 | 3 | 7 | 3 |
| Total |  | 909.3 |  | 909.5 |
| Mineral and vitamin supplement |  |  |  |  |
| Calcium pantothenate (mg) |  | 5,000 |  | 5,000 |
| Manganese (g) |  | 75 |  | 75 |
| Organic arsenical supplement |  | 0.1 |  | 0.1 |
| Selenium (mg) |  | 90.8 |  | 90.8 |
| Zinc (g) |  | 30 |  | 30 |
| Vitamin A (IU) |  | 4,000,000 |  | 4,000,000 |
| Vitamin D (IU) |  | 1,000,000 |  | 1,000,000 |
| Vitamin E (mg) |  | 2,000 |  | 2,000 |
| Vitamin K (mg) |  | 2,000 |  | 2,000 |
| Choline (mg) |  | 503,000 |  | 672,000 |
| Niacin (mg) |  | 20,000 |  | 20,000 |
| Riboflavin (mg) |  | 3,000 |  | 3,000 |
| Vitamin B-12 (mg) |  | 12 |  | 12 |
| Total |  | 2000.9 |  | 2000.1 |

F. Grower/Finisher Turkey Rations

TABLE 18

|  | Grower (8–16 weeks) | | Finisher (16 weeks-market) | |
|---|---|---|---|---|
|  | lbs. | kgs. | lbs. | kgs. |
| Ingredients |  |  |  |  |
| Ground yellow corn | 1194 | 595 | 1490 | 677.2 |
| Wheat middlings | 50 | 23 | — | — |
| Alfalfa meal, 17% | 25 | 11.3 | 25 | 11.3 |
| Soybean meal, dehulled | 570 | 259 | 335 | 152.3 |
| Meat and bone meal, 47% | 50 | 23 | 50 | 23 |
| Dicalcium phosphate | 32 | 14.5 | 23 | 10.5 |
| Ground limestone | 14 | 6 | 17 | 8 |
| Stabilized yellow grease | 45 | 20.7 | 45 | 20.7 |
| CLA Powder | 5 | 2.3 | 5 | 2.3 |
| Iodized Salt | 10 | 4.5 | 10 | 4.5 |
| Total |  | 909.3 |  | 909.3 |
| Mineral and vitamin supplements |  |  |  |  |
| Calcium pantothenate (mg) |  | 4,500 |  | 4,500 |
| Manganese (g) |  | 30 |  | 30 |
| Selenium (mg) |  | 181.6 |  | 181.6 |
| Zinc (g) |  | 30 |  | 30 |
| Vitamin (IU) |  | 1,500,000 |  | 7,500,000 |
| Vitamin D (IU) |  | 1,700,000 |  | 1,700,000 |
| Vitamin E (IU) |  | 10,000 |  | 10,000 |
| Biotin (mg) |  | 100 |  | 100 |
| Choline (mg) |  | 388,000 |  | 417,000 |
| Niacin (mg) |  | 46,000 |  | 48,000 |
| Riboflavin (mg) |  | 5,000 |  | 5,000 |
| Vitamin B-12 |  | 6 |  | 6 |
| Total |  | 2000 |  | 2000 |

G. Dry Dog Food Formula

TABLE 19

| Ingredients | Formula 1, % | Formula 2, % |
|---|---|---|
| Meat and bone meal, 50% CP | 8.0 | 15.0 |
| Fish meal, 60% CP, low fat | 5.0 | 3.0 |
| Soybean meal, 44% CP | 12.0 | — |
| Soybean meal, 50% CP | — | 19.0 |
| Wheat germ meal, 25% CP | 8.0 | 5.0 |
| Skimmed milk, dried | 4.0 | 2.75 |
| Cereal grains, mixed | 51.23 | — |
| Corn, flaked | — | 23.25 |
| Wheat bran | 4.0 | — |
| Wheat, flaked | — | 23.35 |
| Animal fat | 1.75 | 2.75 |
| CLA Powder | .25 | .25 |
| Steamed bone meal | 2.0 | — |
| Brewers yeast | 2.0 | 5.0 |
| Fermentation solubles, dehydrated | 1.0 | — |
| Salt and trace minerals | 0.5 | 0.5 |
| Vitamin mixture | 0.25 | 0.25 |
| Ferric oxide | 0.02 | — |
| Total | 100.00 | 100.00 |

H. Simi-Moist Dog Food Formulas

TABLE 20

| Ingredients | Formula 1, % | Formula 2, % |
|---|---|---|
| Soy flakes | 30.9 | 33.5 |
| Meat byproducts, 70% moisture | 32.0 | — |
| Meat and bone meal, dehydrated | — | 7.3 |
| Water | — | 25.6 |

TABLE 20-continued

| Ingredients | Formula 1, % | Formula 2, % |
|---|---|---|
| Sugar | 21.0 | 21.0 |
| Calcium and phosphorous supplement | 3.3 | — |
| Soybean hulls | 3.1 | 3.1 |
| Skimmed milk, dried | 2.5 | — |
| Propylene glycol | 2.1 | 2.1 |
| Sorbitol | 2.0 | 2.0 |
| Animal fat | .75 | 3.95 |
| CLA Powder | .25 | .25 |
| Emulsifiers | 0.9 | — |
| Potassium sorbate | 0.35 | 0.35 |
| Salt | 0.6 | 0.6 |
| Vitamins | 0.25 | 0.25 |
| Total | 100.000 | 100.000 |

EXAMPLE 11

Large-Scale Preparation of CLA

This example illustrates a method of preparing free fatty acids of CLA on a pilot scale by the isomerization of safflower oil. 1000 kg of KOH was dissolved in 2070 L of propylene glycol. The mixture was then heated to 100° C. with stirring. Next, 2340 L of safflower oil was added and the temperature was elevated to 150° C. for 3 hours. The mixture was then cooled and 1000 L of water and 1350 L of HCL was added. At this point, the solution separated into two layers, with the free fatty acids as the top layer. The layers were separated and the bottom aqueous layer discarded. The top layer was washed with 1000 L of water containing 50 kg of citric acid. The aqueous layer was discarded and the oil (CLA) containing layer was dried under vacuum.

EXAMPLE 12

Production of Triacylglycerides

CLA was prepared according to the method of Example 11. The product was then distilled on a molecular distillation plant at 150° C. and a pressure of $10^{-2}$ mbar. Next, 1000 kg of the distilled product was mixed with 97 kg of pure glycerol and 80 kg lipase. The reaction was allowed to proceed for 12 hours at 55° C. under vacuum and with stirring. The triacylglyceride product was distilled on a molecular distillation apparatus to remove unreacted fatty acids.

EXAMPLE 13

Treatment with Absorbing Agents

A triacyglyceride of CLA was prepared as described in Example 14. The sample was deodorized at 150° C. and 1mm Hg for 3 hours. Next, 500 ml of the sample was treated with powdered silica. Silica was added to 2% and heated to 90–100° C. under vacuum for 30 minutes. The sample was then cooled and filtered.

EXAMPLE 14

Production of CLA with Alcoholate Catalysts

This example describes the production of CLA from safflower oil using potassium methylate as a catalyst. Distilled methyl ester of sunflower oil (41.5 g) was placed in a reactor with 0.207 g methanol and 0.62 g potassium methylate, and the reactor purged with nitrogen before closing. The contents of the reactor were stirred while to 120° C. The reaction was then allowed to proceed at 120° C. for 4 hours. the reactor was then cooled to 80° C. and the contents were transferred to a separating funnel and washed with hot distilled water and then with hot water containing citric acid. The methylester was then dried under vacuum with moderate heat. The dried methyl ester was dissolved in isooctane and analyzed by GLC with a Perkin Elmer autosampler. The column was a highly polar fused silica type. the following program was used:

| | |
|---|---|
| Injection: | Splitless at 250° C. |
| Detection: | Flame ionization detector at 280° C. |
| Carrier: | Helium at psig. |
| Oven program: | 80° C.–130° C. (45° C./min.), then 1° C./min. to 220° C. and 220° C. throughout for 10 min. |
| Column: | WCOT FUSED SILICA 0.25 mm 100 m, CP-SIL 88 for FAME, df + 0.2. |

The CLA obtained consisted almost exclusively of the c9,t11 and t10,c12 isomers of CLA as shown in Table 21.

TABLE 21

CLA Produced by Isomerization with Potassium-Methylate

| Fatty Acid | Before Isomerization | After Isomerization |
|---|---|---|
| C 16:0 | 5.41 | 5.54 |
| C 18:0 | 3.87 | 3.72 |
| C 18:1 | 29.01 | 29.19 |
| C 18:2, c9, c12 | 59.43 | 0.84 |
| CLA, c9, c11 | 0 | 28.84 |
| CLA, t10, c12 | 0 | 28.45 |
| CLA, c9, c11 | 0 | 0.56 |
| CLA, c10, c12 | 0 | 0.40 |
| CLA, t9, t11; t10, t12 | 0 | 0.27 |

EXAMPLE 15

Production of CLA Powder

This example describes the production of a powder containing CLA triglycerides. The CLA triglycerides may be prepared as described above. Warm water (538.2 ml at 110–120° F.) and HI-CAP 100 (approximately 230.9 g, National Starch, Bridgewater, N.J.) are combined and agitated until the dispersion is free of any lumps. CLA triglyceride (230.9 g) is then added and the mixture homogenized for 2 min in an Arde Berinco lab homogenizer at setting 30. The pre-emulsion is then homogenized at full speed for 2–5 min (one pass at 3500 psi total pressure). The particle size is checked and should be from about 0.8 to 1.0 microns. The emulsion is then spray dried in a seven foot conical dryer at the following settings: inlet temperature (190–215° C.); outlet temperature (95–100° C.). Outlet temperature is maintained by adjusting the emulsion feed rate. This process produces a free flowing powder containing approximately 50% CLA triglyceride.

EXAMPLE 16

Production of Powders Containing Other Oils

The method described in Example 15 was repeated, except that TONALIN free fatty acid CLA, flax oil, primrose oil, and borage oil were substituted for the CLA triglycerides. A free flowing powder of approximately 50% of the respective free fatty acids or oils was obtained.

EXAMPLE 17

Production of Powders with Other Encapsulating Agents

The method described in Example 15 was repeated, except that MIRA-CAP (A.E. Stanley) and maltodextrin were substituted for the HI-CAP 100. When tested at a 50% oil load, these agents were not able to produce an emulsion and thus could not be spray dried.

EXAMPLE 18

Production of Powders with Higher Oil Loads

The method described in Example 15 was repeated, except that the oil concentration was increased to 60% or 65%, respectively. The HI-CAP 100 supported formation of an emulsion and produced a free-flowing powder when spray dried. However, the emulsion contained beadlets of up to 10 microns.

What should be clear from above is that the present invention provides a free flowing powder containing a high amount of CLA triglyceride or other oils. The powder can be used in the formulation of animal feeds and in food products suitable for human consumption.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in medicine, biochemistry, or related fields are intended to be within the scope of the following claims.

What is claimed is:

1. A composition comprising a powder of a conjugated linoleic acid moiety selected from the group consisting of CLA fatty acids, CLA triglycerides and CLA alkylesters, wherein said powder is greater than 20% conjugated linoleic acid moiety on a weight/weight basis and wherein said powder comprises an excipient selected from the group consisting of HI-CAP 100 and HI-CAP 200.

2. The composition of claim 1, wherein said conjugated linoleic acid moiety is a CLA triglyceride.

3. The composition of claim 1, wherein said conjugated linoleic acid moiety is selected from the group consisting of a CLA free fatty acid and a CLA alkylester.

4. The composition of claim 1, wherein said powder is greater than 25% conjugated linoleic acid moiety on a weight/weight basis.

5. The composition of claim 1, wherein said powder is greater than 40% conjugated linoleic acid moiety on a weight/weight basis.

6. The composition of claim 1, wherein said powder is greater than 50% conjugated linoleic acid moiety on a weight/weight basis.

7. The composition of claim 1, wherein said powder is free flowing.

8. The composition of claim 1, wherein said powder is odorless.

9. A composition comprising a powder of a conjugated linoleic acid moiety selected from the group consisting of CLA fatty acids, CLA triglycerides and CLA alkylesters, wherein said powder is between about 20% and 65% conjugated linoleic acid moiety on a weight/weight basis and wherein said powder comprises an excipient selected from the group consisting of HI-CAP 100 and HI-CAP 200.

10. The composition of claim 9, wherein said conjugated linoleic acid moiety is a CLA triglyceride.

11. The composition of claim 9, wherein said conjugated linoleic acid moiety is selected from the group consisting of a CLA free fatty acid and a CLA alkylester.

12. The composition of claim 9, wherein said powder is free flowing.

13. The composition of claim 9, wherein said powder is odorless.

14. The composition of claim 1, further comprising a foodstuff.

15. The composition of claim 9, further comprising a foodstuff.

* * * * *